US007022351B2

(12) United States Patent
Abdel-Monem et al.

(10) Patent No.: US 7,022,351 B2
(45) Date of Patent: Apr. 4, 2006

(54) COMPOSITION FOR SUPPLEMENTING ANIMALS WITH SOLUTIONS OF ESSENTIAL METAL AMINO ACID COMPLEXES

(75) Inventors: Mahmoud M. Abdel-Monem, Moscow, ID (US); Michael D. Anderson, Eden Prairie, MN (US)

(73) Assignee: Zinpro Corporation, Eden Prairie, MN (US)

( * ) Notice: Subject to any disclaimer, the term of this patent is extended or adjusted under 35 U.S.C. 154(b) by 279 days.

(21) Appl. No.: 10/341,732

(22) Filed: Jan. 14, 2003

(65) Prior Publication Data

US 2004/0137108 A1 Jul. 15, 2004

(51) Int. Cl.
*A23K 1/00* (2006.01)
*A23L 1/304* (2006.01)

(52) U.S. Cl. .............................. 426/2; 426/74; 426/807
(58) Field of Classification Search .................... 426/2, 426/74, 807
See application file for complete search history.

(56) References Cited

U.S. PATENT DOCUMENTS

| 3,463,858 A | 8/1969 | Anderson .................... 424/289 |
| 3,925,433 A | 12/1975 | Abdel-Monem |
| 3,941,818 A | 3/1976 | Abdel-Monem |
| 3,950,372 A | 4/1976 | Abdel-Monem |
| 4,021,569 A | 5/1977 | Abdel-Monem |
| 4,067,994 A | 1/1978 | Anderson et al. |
| 4,216,143 A | 8/1980 | Ashmead |
| 4,216,144 A | 8/1980 | Ashmead |
| 4,425,280 A | 1/1984 | Ho |
| 4,599,152 A | 7/1986 | Ashmead |
| 4,670,269 A | 6/1987 | Abdel-Monem |
| 4,678,854 A | 7/1987 | Abdel-Monem |
| 4,830,716 A | 5/1989 | Ashmead |
| 4,900,561 A * | 2/1990 | Abdel-Monem et al. ........ 426/2 |
| 4,948,594 A * | 8/1990 | Abdel-Monem et al. ........ 426/2 |
| 4,956,188 A | 9/1990 | Anderson ..................... 426/74 |
| 5,061,815 A * | 10/1991 | Leu ............................ 556/118 |
| 5,139,792 A * | 8/1992 | Ware et al. ..................... 426/2 |
| 5,278,329 A | 1/1994 | Anderson |
| 5,504,055 A | 4/1996 | Hsu |
| 5,516,925 A | 5/1996 | Pedersen et al. |
| 5,583,243 A | 12/1996 | Abdel-Monem |
| 5,698,724 A | 12/1997 | Anderson et al. ............. 556/50 |
| 5,702,718 A | 12/1997 | Ridenour .................... 424/438 |
| 6,012,608 A * | 1/2000 | Ridenour ...................... 222/59 |
| 6,166,071 A | 12/2000 | Ashmead et al. |
| 6,197,815 B1 | 3/2001 | Hsu ........................... 514/502 |

FOREIGN PATENT DOCUMENTS

| EP | 0 377 526 A | 7/1990 |
| FR | 2 539 005 A | 7/1984 |
| WO | WO 03/101436 A1 | 12/2003 |

* cited by examiner

*Primary Examiner*—C. Sayala
(74) *Attorney, Agent, or Firm*—McKee, Voorhees & Sease, P.L.C.

(57) ABSTRACT

A process for preparation of stable, liquid solutions of complexes of trace elements and amino acid complexes of L-lysine, glycine, leucine, and serine. The resulting complexes are used to supplement domestic animals nutritionally. Since the solutions are stable, they can be used as a top drench or in drinking water.

8 Claims, No Drawings

COMPOSITION FOR SUPPLEMENTING ANIMALS WITH SOLUTIONS OF ESSENTIAL METAL AMINO ACID COMPLEXES

FIELD OF THE INVENTION

This invention relates to the field of animal feed supplements and more particularly to the preparation and nutritional value of supplementing the diets of domestic animals with stable solutions of essential metal amino acid complexes.

BRIEF SUMMARY OF THE INVENTION

This invention relates to the development of stable aqueous solutions of trace metal amino acid complexes for use as feed additive in animal nutrition. These compositions are suitable for use in situations where the feed additives are administered to animals as liquids in the drinking water or as a drench. The complexes described in this invention are more effective in meeting the dietary needs of animals than the inorganic salts. The compositions described in this invention have commercial potential because they are stable; can be obtained by practical methods at a reasonable cost and meet a critical need in the field of animal nutrition. They involve a process of controlled pH, preferably the use of L-lysine and/or glycine, and in some cases, solubility enhancers, such as hydroxyl acids like citric acid.

BACKGROUND OF THE INVENTION

The presence of essential metals in sufficient quantities and in a biologically available form in diet is essential for maintaining the health and well being of domestic animals and poultry. Because essential metals such as copper, iron, manganese and zinc are often deficient in common feed ingredients, supplemental amounts of these nutrients are often added to the feed of domesticated animals and poultry. Many commercial feed additives have been developed to provide the essential metals in forms that are readily biologically utilizable. The degree of biological availability of nutrients is often referred to as "bioavailability". Bioavailability of essential metals depends on the physical and/or chemical properties of the form in which the metal is present in the diet. Increased bioavailability of supplemental metals is beneficial because it allows the use of lower concentrations of the metals in the diet to meet the nutritional needs of animals, while lowering the potential harmful effects of high levels of these metals both on the animals and on the environment.

Several commercial products are available in which trace elements are more bioavailable than the corresponding inorganic source of the metal. The enhanced bioavailability is attributed to the association of the metal with an organic molecule, generally known as ligand. This association or bonding results in the increased availability of the metal for utilization by animals, i.e. increased bioavailability. The increased bioavailability of the essential elements in these products is the result of increased solubility, greater stability in the gut, enhanced absorption into circulation and/or improved metabolic utilization.

The common assignee of the present application has in the past synthesized and patented metal complexes of amino acids as a more bioavailable source of the essential elements. The following are examples of these patents: U.S. Pat. Nos. 3,941,818; 3,950,372; 4,021,569; 4,039,681; and 4,067,994 disclose 1:1 complexes of alpha amino acids, preferably DL-methionine with the transition metals zinc, chromium, manganese and iron. The formation of similar complexes with L-methionine is disclosed in U.S. Pat. No. 5,278,329. U.S. Pat. Nos. 4,900,561 and 4,948,594 disclose copper complexes of alpha amino acids containing terminal amino groups. Complexes of copper, manganese, zinc and iron with alpha hydroxyl aliphatic carboxylic acids are disclosed in U.S. Pat. Nos. 4,956,188 and 5,583,243. U.S. Pat. Nos. 4,670,269 and 4,678,854 disclose complexes of cobalt with poly-hydroxyl carboxylic acids such as glucoheptanoic acid. Complexes of the amino acid L-lysine with trace elements are disclosed in U.S. Pat. No. 5,061,815. The effectiveness of the compounds disclosed in these patents has been demonstrated from data provided in some of these patents and in numerous scientific publications and technical reports.

The above patents describe the use of pure synthetic or natural amino or hydroxyl acids. In U.S. Pat. No. 5,698,724 the assignee of the current application disclosed the synthesis of complexes of essential elements with natural amino acids obtained by the hydrolysis of proteins. Since this patent was issued, a large number of field studies have demonstrated that metals from these complexes are more bioavailable than metals from inorganic sources.

The commercial products based on the above cited patents are available as solids for addition to solid feed. These solids are either carrier-free products or products in which the material is mixed on a carrier. The advantages of using solid feed additives are numerous and include convenience of handling, shipping and storage, lower costs of shipping, stability of the complexes in the dry state and finally ease of blending the solids in the other solid feed ingredients. A method for preparing an aqueous composition containing a metal-amino acid complex and directly applying the aqueous composition to solid feed is described in U.S. Pat. No. 5,702,718. The aqueous composition of metal-amino acid complexes as described in U.S. Pat. No. 5,702,718 is often unstable resulting in the formation of a heavy precipitate. To deal with the difficulties associated with measuring and dispensing the heterogeneous products described in U.S. Pat. No. 5,702,718, the inventor filed and was granted U.S. Pat. No. 6,012,608 which describes a method and apparatus for "local storage, metering and dispensing of a material such as a supersaturated fluid feed supplement, for example, the zinc methionine supersaturated feed supplement disclosed in U.S. Pat. No. 5,702,718".

In some animal feeding operations, the trace metal additives are administered as an aqueous liquid alone or in conjunction with other nutrients such as electrolytes. Typically, the additives are administered to animals by using a drench system or in the drinking water in a trough. In the drench system the additives are administered directly into the animal's mouth. Most drench systems are electronically controlled and consist of a holding tank in which the liquids are continuously agitated or circulated to prevent products from settling. The drench liquid is pressurized through a delivery device into the animal's mouth. The amount of liquid dispensed is controlled by the length of time the delivery device is pressurized. The trough treatment method involves the dispensing of the liquid additives into the drinking water. This is accomplished by the use of in-line dispensers that meter the liquid additive in the watering system.

The preparation of a liquid additive of the essential metal-amino acid complexes represents special challenges, especially if a homogenous solution is required. The 1:2 metal-amino acid complexes are generally insoluble in water and can be formulated only as heterogeneous suspensions. Although several suspending agents are available for preparing relatively stable suspensions, these suspension must be continuously agitated or circulated if a uniform dosing is required. The 1:1 metal-amino acid complexes are usually soluble in water. However, if the solution is allowed to stand the complex gradually breaks down with the precipitation of the metal and/or the amino acid. The rate of precipitate formation depends on the concentration of the complex in the original solution and solubility of the constituent amino acid and metal. This behavior is best illustrated by the metal complexes of the amino acid methionine. A solution of the metal-methionine complex is stable at high temperatures. However, upon standing the methionine because of its low water solubility begins to form crystals which results in further degradation of the complex and formation of a heterogeneous mixture of the methionine crystals and a supernatant containing some metal-methionine complex and the inorganic salt of the metal. This is demonstrated in Examples 1. The formation of a heterogeneous product of the liquid supplements was anticipated in U.S. Pat. No. 5,702,718 as demonstrated by the inventor's statement in U.S. Pat. No. 6,012,608 that a feed supplement such as zinc methionine "is typically a supersaturated liquid (20% or greater solid matter) and, if it is allowed to remain motionless, it may " settle" and form a partial solid which may be very difficult to circulate and apply as a liquid to other feed components". We have examined several commercial samples of products labeled as covered by U.S. Pat. No. 5,702,718. Example 2, describes a typical analysis of one of these products. The results in Example 2 indicate that these products are indeed heterogeneous mixtures containing an insoluble precipitate that is made predominantly of methionine, and a liquid phase that contains zinc and methionine.

The preparation of a stable homogenous composition that contains water-soluble metal amino acid complexes requires the careful selection of the amino acid. The formulation of such product must optimize the solubility of the complex without impinging on its stability. The pH of such a composition must be maintained within an optimum range and all substances that may initiate or accelerate the decomposition of the complex and the precipitation of the metal and/or the amino acid must be eliminated from the product. The purpose of the present invention is to describe the composition and methods of preparation of stable aqueous solutions of metal amino acid complexes for use as feed additives in animal nutrition.

DETAILED DESCRIPTION OF THE INVENTION

It is now well established that essential metals are more bioavailable from amino acid complexes than from inorganic forms of the metal. The vast majority of metal-amino acid complexes are commercially available as solid mixtures for addition to a solid feed. These solids are either carrier-free products or products in which the material is mixed on a carrier. In some feeding operations, the trace metal additives are administered as an aqueous liquid alone or in combination with other nutrients such as electrolytes. However, the preparation of a liquid composition of the metal-amino acid complexes represents special challenges because of the fundamental chemical properties of these complexes, especially if a stable solution is required. When the salt of an essential metal is mixed with a solution of the amino acid, equilibrium is established between the various species of the amino acid including the metal-amino acid complexes. The relative concentrations of these species depend on the pH of the solution, the concentration of the amino acid, the concentration of the metal and the stability constants of the metal-amino acid complexes and the pKa of the amino acid. At high hydrogen ion concentrations, i.e. low pH the protonated form of the amino acids predominate and the metal-amino acid complex is present only at a relatively low concentrations. The exact lower limit of hydrogen ion concentration where the concentration of the metal-amino acid complex becomes of no practical value depends on the pKa of the amino acid and the metal. However, we found that solutions at pH>2 generally contains measurable concentrations of the metal-amino acid complexes. Only copper-amino acid complexes are present in practical levels at pH<2. At low hydrogen ion concentrations, i.e. high pH, the 1:2 metal-amino acid complexes begin to form as well as metal hydroxides. Metal hydroxides and 1:2 metal-amino acid complexes are sparingly soluble in water. The behavior of metal-amino acid complexes described above indicates that there is a narrow range of pH where the 1:1 metal-amino acid complexes exit in optimum concentrations. This range is between pH 2 and pH 6 for most metals and amino acids.

Another challenge that complicates the preparation, shipping and storage of an aqueous solution of the metal-amino acid complexes is the solubility of the Zwitter ionic form of the amino acid in water. A solution of the metal-amino acid complex that is formulated to have a pH between 2 and 5 may not be stable because of the precipitation of the amino acid. In such a solution the Zwitter ion form of the amino acid is present in a very low concentration in equilibrium with the metal-amino acid complex. If this form of the amino acid has low water solubility, a supersaturated solution is formed. As the conditions change, such as cooling or the introduction of particulate matter that can serve as a seed for crystal formation, the amount of the amino acid that is present above the saturation level will begin to crystallize in the form of a precipitate. This will result in a shift in the equilibrium that results in the decomposition of the metal-amino acid complex to form additional amounts of the free amino acid and metal to restore the concentrations of the different species to maintain the equilibrium. This results in further precipitation of the amino acids.

Efforts to prepare a homogenous liquid composition of zinc-methionine complex were unsuccessful because of the precipitation of methionine and decomposition of the complex. The heterogeneous liquid obtained was primarily a mixture of crystalline methionine and a solution containing zinc salt and low concentration of the zinc-methionine complex. Similarly, methionine complexes of other metals were unstable and produced heterogeneous liquids. Example 1 summarizes the results obtained in an experiment for the preparation of a liquid composition of zinc-methionine.

Some liquid compositions containing metal-amino acid complexes are commercially available. We have obtained samples of some of these commercial products and carefully analyzed their contents. Example 2 summarizes the results of such analysis. Similar to samples prepared in our laboratory, these products are mixtures of crystalline methionine and a solution of zinc salt and zinc-methionine complex.

The present invention describes compositions that contain stable water soluble metal-amino acid complexes for use in animal nutrition. The formulation of these compositions required consideration of three critical factors. These factors are: the selection of the amino acid, pH adjustment of the final solution and the use of additives to increase the solubility or stability of the metal-amino acid complex. The formulation of each of the compositions covered by this invention required extensive experimentations to identify the conditions that provided optimum results.

Several factors were considered in the selection of the amino acid including solubility in water, commercial availability, cost, stability in solution and the stability of its complexes with the essential metals. Two natural amino acids were found to provide the best results, L-lysine and glycine. This is because these amino acids are readily soluble in water in the most desirable pH range of 2.5–4.5. Additionally, these two amino acids are commercially readily available at a reasonable cost. Other amino acids that are also suitable include leucine and serine, but these amino acids are not commercially readily available at a reasonable cost at this time.

The pH of the compositions described in this invention was maintained between 2.0–6.0 but most preferably between pH 2.5–4.5. This is the range for optimum stability of the 1:1 metal-amino acid complexes. At a pH lower than 2.5, the amino acid is predominantly in the protonated form and the concentration of the metal-amino acid complexes is low. At pH greater than 4.5, the 1:2 metal amino acid complexes begin to form in measurable concentrations which may result in precipitate formation. When necessary, the pH of the solution was adjusted by the careful addition of a diluted base. In general, bases such as ammonium hydroxide were found to be more suitable than strong bases such as sodium hydroxide. Other suitable bases include basic amino acids such as Lysine and alkyl amines such as ethanol amine. The temperature of the solution must be controlled during the addition of the base to prevent the formation of a precipitate of the metal hydroxides that may be difficult to re-dissolve. In general, the temperature must be maintained below 50° C. and preferably between 30° C. and 40° C.

In few cases it was not possible to obtain a stable water-soluble metal-amino acid solution without the use of an additive to increase the stability and solubility of the complexes. This was especially the case with metal complexes of Fe (III). Citric acid was the most effective additive we found. Other hydroxyl acids such as tartaric, gluconic and glucoheptanoic were also effective but to a lesser degree. The amount of added hydroxyl acid should be from 0.5 to 1.0, preferably 0.6 to 0.8 molar equivalents to the amount of metal used.

The following examples are offered to illustrate the practical methods of obtaining these compositions, their physical and chemical properties, and their use as a source of trace elements in animal nutrition.

EXAMPLE 1

Attempted Preparation of a Solution of Zine-Methionine Complex

A solution of zinc sulfate (92.371 g, 0.32 moles) in water (90 ml) was prepared by the aid of gentle heat and stirring. DL-Methionine (48.656 g, 0.32 moles) was added to the solution and heating with stirring was continued until a clear solution was formed. The solution was cooled and completed to 200 ml. White crystals began to form on standing. The mixture was allowed to stand at room temperature for 72 hours and filtered under reduced pressure. The precipitate was dried in an oven at 80° C. for 18 hours. The filtrate was carefully transferred into a 250-ml volumetric flask and the filtration flask was washed with three successive 20 ml portions of water. The washings were transferred into the volumetric flask and completed to volume. The zinc and methionine contents of the precipitate and filtrate were determined separately. The results are summarized in Table 1. The FTIR of the precipitate in a potassium bromide pellet was recorded.

TABLE 1

| Precipitate | |
|---|---|
| Weight of Precipitate (g) | 49.168 |
| Methionine Content, % | 97.29 |
| Wt. Methionine in Precipitate, (g) | 47.8355 |
| % Recovery of methionine | 98.3138 |
| Zinc Content, % | 5.09 |
| Wt. of Zinc in Precipitate, (g) | 2.5027 |
| Filtrate | |
| Methionine Content, (g) | 3.6500 |
| Zinc Content, (g) | 18.34 |
| Total | |
| Total Methionine Found, (g) | 51.4855 |
| % of total methionine in precipitate | 92.911 |
| % of total methionine in filtrate | 7.089 |
| % Methionine in sample | 25.74 |
| Total Zinc Found, (g) | 20.8427 |
| % of total zinc in precipitate | 12.01 |
| % of total zinc in filtrate | 87.99 |
| % Zinc in Sample | 10.42 |
| Maximum Bound Zinc in precipitate, (g) | 2.5027 |
| Maximum Bound Zinc in filtrate, (g) | 1.5993 |
| Total Maximum Bound Zinc in sample, (g) | 4.1020 |
| Maximum Bound Zinc in sample, % | 2.05 |
| Maximum of found zinc is bound, % | 19.68 |
| Maximum of label claim zinc is bound, % | 20.51 |

The FTIR spectrum of the dried precipitate obtained after filtration of the sample was examined. The FTIR spectrum was recorded in a Potassium Bromide Pellet using a Shimadzu FTIR-8300 Fourier Transform Infrared Spectrophotometer. The spectrum showed absorptions at 2948.9 (s), 2914.2 (s), 2729.1 (m), 2619.1 (m), 2102.3 (w), 1654.8 (s), 1620.1 (s), 1583.4 (vs), 1515.9 m), 1415.7 (s), 1338.5 (s), 1163.0 (m), 1082.0 (m), 925.8 (w), and 551.6 (m) cm$^{-1}$. This spectrum is identical to that of an authentic sample of DL-methionine.

These results indicate that the zinc-methionine complex is not stable in this preparation. The product is a suspension of methionine in a solution of zinc salt and zinc-methionine complex.

EXAMPLE 2

Evaluation of a Commercial Zinc-Methionine Liquid Product

An aliquot of a commercial sample of liquid zinc-methionine complex was accurately weighed by difference and filtered by suction through a tarred Whatman Filtercup vacuum filtration funnel (Whatman #1600004, 70 mm dia., 250 ml capacity fitted with #4 grade cellulose filter). The precipitate was dried in an oven at 70–75° C. for 12 hours. The filtrate was carefully transferred into a 250-ml volumetric flask. The filter flask was washed with 3 successive 25 ml of water and the washings were added to the volumetric flask. The filtrate was completed to volume with water. The zinc and methionine contents of the precipitate and diluted filtrate were determined. The results are summarized in Table 2.

TABLE 2

| Weight of Sample Used (g) = Precipitate | 15.314 |
|---|---|
| Weight of Precipitate (g) | 4.309 |
| Precipitate as % of Total, | 28.14 |
| Methionine Content, % | 86.62 |
| Wt. Methionine in Precipitate, (g) | 3.7325 |
| Zinc Content, % | 1.20 |
| Wt. of Zinc in Precipitate, (g) | 0.0516 |
| Filtrate | |
| Methionine Content, (g) | 0.5850 |
| Zinc Content, (g) | 1.2484 |
| Total | |
| Total Methionine Found, (g) | 4.3175 |
| % of total methionine in precipitate | 86.450 |
| % of total methionine in filtrate | 13.550 |
| % Methionine in sample | 28.193 |
| Total Zinc Found, (g) | 1.3000 |
| % of total zinc in precipitate | 3.97 |
| % of total zinc in filtrate | 96.03 |
| % Zinc in Sample | 8.49 |
| Maximum Bound Zinc in precipitate, (g) | 0.0516 |
| Maximum Bound Zinc in filtrate, (g) | 0.2563 |
| Total Maximum Bound Zinc in sample, (g) | 0.3080 |
| Maximum Bound Zinc in sample, % | 2.01 |
| Maximum of found zinc is bound, % | 23.69 |
| Maximum of label claim zinc is bound, % | 20.11 |

The FTIR spectrum of the dried precipitate obtained after filtration of the sample was examined. The FTIR spectrum was recorded in a Potassium Bromide Pellet using a Shimadzu FTIR-8300 Fourier Transform Infrared Spectrophotometer. The spectrum showed absorptions at 2956.7 (s), 2914.2 (s), 2736.8 (m), 2626.9 (m), 2092.6 (w), 1654.8 (s), 1620.1 (s), 1579.6 (vs), 1515.9 m), 1415.7 (s), 1338.5 (s), 1280.6 (m), 1157.2 (m), 1107.1 (m), 1082.0 (m), 925.8 (w), 619.1 (w), and 551.6 (m) cm$^{-1}$. This spectrum was identical to that of an authentic sample of DL-methionine.

An aliquot of the filtrate was mixed with FTIR grade Potassium Bromide and dried in a hot air oven. A pellet was formed from the dried mixture and its spectrum was recorded using the Shimadzu FTIR-8300 Spectrophotometer. The spectrum showed absorptions at 3508.3 (s), 3161.1 (s), 2152.4 (w), 2092.6 (w), 1633.6 (s), 1616.2 (s), 1473.5 (m), 1409.9 (m), 1334.6 (m), 1153.3 (vs), 1103.2 (vs), 1010.6 (s), 657.7 (m), 611.4 (s) cm$^{-1}$. This spectrum is consistent with a mixture of methionine and zinc-methionine complex. The peaks at 3508.3, 3161.1, 1633.6, 1473.5, 1409.9, and 1334.6 cm$^{-1}$ are characteristic of the zinc-methionine complex. The peaks at 2092.6, 1616.2, and 1103.2 cm$^{-1}$ are due to the presence of free methionine.

These results indicate that this commercial product is composed of a suspension of methionine in a solution of soluble zinc salt and zinc-methionine complex. The maximum amount of zinc-methionine complex is 20–23% of the total zinc in the sample.

EXAMPLE 3

Preparation and Evaluation of a Solution of Zinc-L-Lysine Complex

Zinc Sulfate Heptahydrate (59.287 g, 0.2 moles) was dissolved in 80 ml of water by the aid of gentle heating and stirring. L-Lysine Monohydrochloride (36.722 g, 0.196 moles) was added to the zinc sulfate solution. Heating and stirring was continued until a clear solution was obtained. The solution was cooled and completed to 125 ml.

| Analysis | Theory | Found |
|---|---|---|
| pH | | 4.449 |
| Specific Gravity | | 1.3165 |
| Zinc Content (EDTA Titration) % | 10.55 | 10.92 |
| Lysine Content (HPLC) % | 23.58 | 24.25 |

The solution was stored in a capped polyethylene bottle for 18 months and reexamined. The product did not change after 18 months. It remained clear and contained 10.97% zinc.

EXAMPLE 4

Preparation and Evaluation of a Solution of Manganese-L-Lysine Complex

Manganese chloride tetrahydrate (40.189 g, 0.2 moles) was dissolved in 60 ml of water by the aid of gentle heating and stirring. L-Lysine Monohydrochloride (36.719 g, 0.196 moles) was added to the manganese chloride solution. Heating and stirring was continued until a clear solution was obtained. The solution was cooled and completed to 104 ml.

| Analysis | Theory | Found |
|---|---|---|
| pH | | 4.804 |
| Specific Gravity | | 1.2789 |
| Manganese Content (EDTA Titration) % | 10.63 | 10.66 |
| Lysine Content (HPLC) % | 28.27 | 31.46 |

The solution was stored in a capped polyethylene bottle for 18 months and reexamined. The product did not change after 18 months. It remained clear and contained 10.62% manganese.

EXAMPLE 5

Preparation and Evaluation of a Solution Copper-L-Lysine Complex

L-Lysine Monohydrochloride (21.562 g, 0.1151 moles) was added to 80 ml of water. The mixture was heated to 40° C. with stirring. Sodium hydroxide (12.805 g of a 25% solution, 0.08 moles) was added. The temperature of the mixture was maintained <40° C. and stirring was continued. Copper sulfate pentahydrate (30.265 g, 0.12 moles) was added. Heating and stirring was continued until a clear solution was obtained. The solution was cooled and completed to 115 ml.

| Analysis | Theory | Found |
|---|---|---|
| pH | | 3.030 |
| Specific Gravity | | 1.2060 |
| Copper Content (Iodometric Titration) % | 6.71 | 6.81 |
| Copper Lysine Content (HPLC) % | 21.53 | 21.40 |

The solution was stored in a capped polyethylene bottle for 18 months and reexamined. The product did not change after 18 months. It remained clear and contained 6.81% copper.

EXAMPLE 6

Preparation and Evaluation of a Solution of Copper-Glycine Complex

Copper Sulfate pentahydrate (50.997 g, 0.2 moles) was dissolved in 60 ml of water by the aid of gentle heating and stirring. Glycine (15.328 g, 0.2 moles) was added to the copper sulfate solution. Heating and stirring was continued until a clear solution was obtained. The solution was cooled and completed to 100 ml.

| Analysis | Theory | Found |
|---|---|---|
| pH | | 3.084 |
| Specific Gravity | | 1.3536 |
| Copper Content (Iodometric Titration) % | 12.73 | 12.78 |

The solution was stored in a capped polyethylene bottle for 18 months and reexamined. The product did not change after 18 months. It remained clear and contained 13.20% copper.

EXAMPLE 7

Preparation and Evaluation of a Solution of Iron-L-Lysine Complex

Ferrous Sulfate pentahydrate (55.608 g, 0.2 moles) was dissolved in 60 ml of water by the aid of gentle heating and stirring. L-Lysine Monohydrochloride (36.718 g, 0.2 moles) was added to the ferrous sulfate solution. Heating and stirring was continued until a clear solution was obtained. The solution was cooled and completed to 106 ml.

| Analysis | Theory | Found |
|---|---|---|
| pH | | 4.328 |
| Specific Gravity | | 1.3334 |
| Iron Content (Colorimetric Assay) % | 10.54 | 10.64 |

The solution was stored in a capped polyethylene bottle for 18 months and reexamined. The product did not change after 18 months. It remained clear and contained 9.33% iron.

EXAMPLE 8

Preparation and Evaluation of a Solution of Iron-Glycine Complex

Ferrous Chloride Tetrahydrate (39.772 g, 0.2 moles) was dissolved in 50 ml of water by the aid of gentle heating and stirring. Glycine (15.329 g, 0.2 moles) was added to the ferrous chloride solution. Heating and stirring was continued until a clear solution was obtained. The solution was cooled and completed to 100 ml.

| Analysis | Theory | Found |
|---|---|---|
| pH | | 3.893 |
| Specific Gravity | | 1.2952 |
| Iron Content (Colorimetric Assay) % | 12.41 | 12.95 |

The solution was stored in a capped polyethylene bottle for 18 months and reexamined. The product did not change after 18 months. It remained clear and contained 12.28% iron.

EXAMPLE 9

Preparation and Evaluation of a Solution of Metals-L-Lysine Complexes

L-Lysine Monohydrochloride (35.481 g, 0.1894 moles) was added to 50 ml of water. The mixture was heated to 40° C. with stirring. Zinc Sulfate Monohydrate (17.761 g, 0.096 moles), manganese sulfate monohydrate (17.546 g, 0.063 moles) and copper sulfate pentahydrate (9.075 g, 0.036 moles) were added successively. Heating and stirring was continued until a clear dark blue solution was obtained. Cobalt chloride solution (1.82 g of a 12.3% cobalt solution, 0.0038 moles) was mixed with sodium glucoheptanoate (1.737 g, 0.007 moles) and the mixture was added to the metals-lysine solution. The solution was cooled and completed to 130 ml.

| Analysis | Theory | Found |
|---|---|---|
| pH | | 3.416 |
| Specific Gravity | | 1.3077 |
| Zinc Content (ICP/AES) % | 4.83 | 4.83 |
| Manganese Content (ICP/AES) % | 2.66 | 2.68 |
| Copper Content (ICP/AES) % | 1.76 | 1.80 |
| Cobalt Content (ICP/AES) % | 0.17 | 0.17 |

The solution was stored in a capped polyethylene bottle for 18 months and reexamined. The product did not change after 18 months. It remained clear and contained 1.80% copper.

EXAMPLE 10

Evaluation of the Effect of Daily Treatment of Cows with a Solution of Zinc-Lysine Complex on Milk Quality Sixty Friesian cows were assigned to a study to determine the effect of the daily oral administration of Zinc L-Lysine complex on milk quality and reproduction. One month prior to calving cows in the treatment group began receiving 400 mg of zinc per head per day from zinc L-lysine. At calving, cows were managed under intensive grazing and received 400 mg of zinc per day from a daily oral drench of zinc L-lysine. Control cows received similar forage and dietary supplements as the treatment cows with the exception of supplemental zinc. Cows received the dietary treatments until 21 weeks postcalving. The effects of zinc L-lysine administration on milk production, composition and quality are summarized in Table 3.

TABLE 3

| | Treatment | |
|---|---|---|
| Response | Control | Zinc L-Lysine |
| Milk production, kg/d | 23.2 | 24.1 |
| Fat yield, kg/d | 1.12 | 1.17 |
| Protein yield, kg/d | 0.77 | 0.78 |
| Fat, % | 4.83 | 4.87 |
| Protein, % | 3.33 | 3.25 |
| Somatic cell count, 1,000 s/ml | 145 | 85 |
| Serum zinc, µmol/L | 12.6 | 14.6 |

TABLE 3-continued

| | Treatment | |
|---|---|---|
| Response | Control | Zinc L-Lysine |
| Serum copper, μmol/L | 11.0 | 10.4 |
| Days to first oestrus | 38.5 | 34.5 |
| Services/conception | 1.3 | 1.4 |
| Calving to conception, days | 84.1 | 87.8 |
| % pregnant | 86.7 | 93.3 |

The results summarized in Table 3 indicate that cows receiving liquid zinc L-lysine complex produced 0.9 kg/day more milk with 41.38% lower somatic cell count compared to cows that did not receive the zinc L-lysine complex.

EXAMPLE 11

Evaluation of the Effects of Daily Treatment of Intensely Grazed Cattle with a Solution of Multi-Metal-Lysine Complex on Lactation, Mastitis, Reproduction, and Claw Integrity Five hundred fifty five non-lactating Holstein-Friesian cows on a commercial dairy farm were assigned to a study to determine the effects of a solution of multi-metal L-lysine complexes on lactation and reproductive performance. The solution supplied 360 mg zinc from zinc L-lysine complex, 200 mg manganese from manganese L-lysine complex, 125 mg copper from copper L-lysine complex, and 12 mg cobalt from cobalt glucoheptanoate. At 35 days prior to calving, cows were split into 2 groups and intensely grazed on separate paddocks. Cows were fed 0.5 kg/day of a commercial concentrate. The cows in the treatment group received the same concentrate with the exception that it contained the multi-metal L-lysine complexes. After calving, the multi-metal L-lysine complexes solution was added to water of treated cows. The effects of this treatment are summarized in Table 4.

TABLE 4

| | Treatment | |
|---|---|---|
| Response | Control | Multi-metal-L-lysine |
| Milk production, kg/d | 16.6 | 17.5 |
| Fat yield, kg/d | 0.73 | 0.78 |
| Protein yield, kg/d | 0.58 | 0.62 |
| Solids, kg/d | 1.31 | 1.39 |
| Fat, % | 4.44 | 4.49 |
| Protein, % | 3.51 | 3.55 |
| Solids, % | 7.94 | 8.03 |
| Mastitis cases, % | 29.9 | 23.8 |
| Somatic cell count, 1,000 s/ml | 126 | 110 |
| Liver Concentrations, fresh weight | | |
| Zinc, mg/kg, 45 d postpartum | 36.0 | 41.0 |
| Zinc, mg/kg, 165 d postpartum | 39.0 | 52.0 |
| Copper, μmol/kg, 45 d postpartum | 88 | 181 |
| Copper, μmol/kg, 165 d postpartum | 275 | 673 |
| Manganese, mg/kg, 45 d postpartum | 5.3 | 5.7 |
| Manganese, mg/kg, 165 d postpartum | 4.3 | 4.3 |
| Serum concentration, pmol/L | | |
| Vitamin B12, 45 d postpartum | 246 | 334 |

TABLE 4-continued

| | Treatment | |
|---|---|---|
| Response | Control | Multi-metal-L-lysine |
| Vitamin B12, 165 d postpartum | 247 | 379 |
| Empties, % | 18 | 13 |
| Pregnancy rate, % | 82 | 87 |

The results in Table 4 indicate that the cows receiving the soluble multi-metal L-lysine complexes produced 5.4% more milk, 5.8% more energy-corrected milk and 6.3%. more fat-corrected milk. They also produced 6.1% more fat, 6.9% more protein and 6.1% more solids. There was a reduction in mastitis cases and a 38.5% reduction in progesterone vaginal implant given to non-cycling cows (Controlled Internal Drug Releasing, CIDR). There was no effect on liver and manganese concentrations, but liver copper and serum vitamin $B_{12}$ concentrations at 45 and 165 d postpartum were increased.

As can be seen from the above examples, an effective stable, solution of these metal amino-acid complexes has been prepared, that is easily administered to provide yield result of economic benefit to the owners of the treated livestock. Therefore, the invention accomplishes at least the stated objectives.

It goes without saying that certain modification of process conditions, and administration teachings can be made without departing from the spirit and scope of the invention.

What is claimed is:

1. A process of preparing a trace mineral, stable aqueous solution complex, comprising:
   dissolving a trace mineral salt in water that is below 50° C.;
   adding a 1:1 complex forming sufficient amount of an amino acid selecting from the group consisting of L-lysine, glycine, leucine and serine to the trace mineral salt in water; and
   adjusting the pH to within the range of 2.0 to 6.0 to provide a solution that is stable in storage up to at least 18 months.

2. The process of claim 1 wherein the trace mineral is selected from the group consisting of zinc, iron, manganese, chromium, and copper.

3. The process of claim 1 wherein the temperature is maintained between 30° C. and 40° C.

4. The process of claim 1 wherein an additional step is the addition of a small solubilization enhancing effective amount of a hydroxy acid.

5. The process of claim 4 wherein the hydroxy acid is selected form the group consisting of citric acid, tartaric acid, gluconic acid and glucoheptanoic acid.

6. The process of claim 5 wherein the amount of hydroxy acid is from 0.5 to 1.0 molar equivalents to the amount of metal.

7. The process of claim 5 wherein the amount of hydroxy acid is from 0.6 to 0.8 molar equivalents to the amount of metal.

8. The process of claim 1 wherein the pH adjustment is with a mild base selected from the group consisting of ammonium hydroxides and basic amino acids.

\* \* \* \* \*